(12) United States Patent
Flemming et al.

(10) Patent No.: US 8,492,315 B2
(45) Date of Patent: *Jul. 23, 2013

(54) METHOD OF PROVIDING A PATTERN OF BIOLOGICAL-BINDING AREAS FOR BIOLOGICAL TESTING

(75) Inventors: Jeb H. Flemming, Albuquerque, NM (US); Colin T. Buckley, Albuquerque, NM (US); Carrie Schmidt, Las Lunas, NM (US)

(73) Assignee: Life Bioscience, Inc., Albuquerque, NM (US)

( * ) Notice: Subject to any disclaimer, the term of this patent is extended or adjusted under 35 U.S.C. 154(b) by 1092 days.

This patent is subject to a terminal disclaimer.

(21) Appl. No.: 12/200,894

(22) Filed: Aug. 28, 2008

(65) Prior Publication Data
US 2009/0069193 A1  Mar. 12, 2009

Related U.S. Application Data

(60) Provisional application No. 60/968,325, filed on Aug. 28, 2007.

(51) Int. Cl.
*C40B 50/18* (2006.01)

(52) U.S. Cl.
USPC ............. 506/32; 506/9; 427/309; 430/323

(58) Field of Classification Search
None
See application file for complete search history.

(56) References Cited

U.S. PATENT DOCUMENTS

| | | | |
|---|---|---|---|
| 2,515,940 A | 7/1950 | Stookey | |
| 2,515,941 A | 7/1950 | Stookey | |
| 2,628,160 A | 2/1953 | Stookey | |
| 2,684,911 A | 7/1954 | Stookey | |
| 2,971,853 A | 2/1961 | Stookey | |
| 3,985,531 A | 10/1976 | Grossman | |
| 4,788,165 A | 11/1988 | Fong et al. | |
| 5,078,771 A | 1/1992 | Wu | |
| 5,212,120 A | 5/1993 | Araujo et al. | |
| 5,374,291 A | 12/1994 | Yabe et al. | |
| 6,383,566 B1 | 5/2002 | Zagdoun | |
| 6,485,690 B1 | 11/2002 | Pfost et al. | |
| 6,678,453 B2 | 1/2004 | Bellman et al. | |
| 6,783,920 B2 | 8/2004 | Livingston et al. | |
| 6,824,974 B2 | 11/2004 | Pisharody et al. | |
| 6,932,933 B2 | 8/2005 | Helvajian et al. | |
| 7,033,821 B2 | 4/2006 | Kim et al. | |
| 7,132,054 B1 | 11/2006 | Kravitz et al. | |
| 7,179,638 B2 | 2/2007 | Anderson et al. | |
| 7,306,689 B2 | 12/2007 | Okubora et al. | |
| 7,326,538 B2 | 2/2008 | Pitner et al. | |
| 7,407,768 B2 | 8/2008 | Yamazaki et al. | |
| 7,470,518 B2 | 12/2008 | Chiu et al. | |
| 7,497,554 B2 | 3/2009 | Okuno | |
| 8,062,753 B2 | 11/2011 | Schreder et al. | |
| 8,096,147 B2 | 1/2012 | Flemming et al. | |
| 2003/0025227 A1 | 2/2003 | Daniell | |
| 2003/0124716 A1 | 7/2003 | Hess et al. | |
| 2003/0135201 A1 | 7/2003 | Gonelli | |
| 2004/0198582 A1 | 10/2004 | Borrelli et al. | |
| 2006/0159916 A1 | 7/2006 | Dubrow et al. | |
| 2006/0171033 A1* | 8/2006 | Schreder et al. | 359/566 |
| 2006/0188907 A1 | 8/2006 | Lee et al. | |
| 2006/0234298 A1* | 10/2006 | Chiu et al. | 435/7.1 |
| 2008/0182079 A1* | 7/2008 | Mirkin et al. | 428/195.1 |
| 2008/0248250 A1 | 10/2008 | Flemming et al. | |
| 2010/0022416 A1 | 1/2010 | Flemming et al. | |
| 2011/0170273 A1 | 7/2011 | Helvajian | |

FOREIGN PATENT DOCUMENTS

| | | | |
|---|---|---|---|
| CN | 1562831 A | * | 1/2005 |
| JP | 08026767 | | 1/1996 |
| WO | 2008119080 | | 10/2008 |

OTHER PUBLICATIONS

Zhang et al (2003 Nanotechnology 14:1113-1117).*
International Search Report and Written Opinion for PCT/US2008/074699 dated Feb. 2009.
Aslan, et al, "Metal-Enhanced Fluorescence: an emerging tool in biotechnology" Current opinion in Biotechnology (2005), 16:55-62.
Chowdhury, et al, "Metal-Enhanced Chemiluminescence", J Fluorescence (2006), 16:295-299.
"Covalent Coupling" TechNote #205, Bangs Laboratories, www.bangslabs.com/technotes/205.pdf.
Geddes, et al, "Metal-Enhanced Fluorescence" J Fluorescence, (2002), 12:121-129.
Lakowicz, et al; "Advances in Surface-Enhanced Fluorescence", J Fluorescence, (2004), 14:425-441.

* cited by examiner

*Primary Examiner* — Christopher M Gross
(74) *Attorney, Agent, or Firm* — Chainey P. Singleton; Chalker Flores, LLP

(57) ABSTRACT

The present invention provides a method of forming one or more biological-binding areas on a substrate for biological-testing. The method includes activating at least a portion of a glass-ceramic substrate comprising glass and one or more metal containing compounds. The one or more metal containing compounds have a range of diameters that are less than about 300 nanometers in diameter and are spaced an average distance of at least one-half the midpoint of the diameter range apart. The one or more metals include compounds selected from metal oxides, metal nanoparticles, metal alloys, and atomic metals. The glass-ceramic substrate is heated to a temperature near the glass transformation temperature to form one or more metal nanoparticles in one or more ceramic biological-binding areas. The glass-ceramic substrate is etched to expose one or more metal. One or more biological molecules are contacted with one or more ceramic biological-binding areas to provide one or more biological testing areas with an increased binding area as compared to un-activated areas.

15 Claims, 2 Drawing Sheets

METHOD OF PROVIDING A PATTERN OF BIOLOGICAL-BINDING AREAS FOR BIOLOGICAL TESTING

CROSS-REFERENCE TO RELATED APPLICATIONS

This application claims priority to U. S. Patent Application Ser. No. 60/968,325 filed on Aug. 28, 2007. This application is related to U. S. patent applications Ser. Nos. 12/058,608 and 12/058,588 filed on Mar. 28, 2008, U. S. Patent Application Ser. No. 60/908,631 filed on Mar. 3, 2007 and U.S. Patent Application Ser. No. 60/910,257 filed on Apr. 5, 2007, the entire contents of all applications are incorporated herein by reference.

TECHNICAL FIELD OF THE INVENTION

The present invention relates in general to the field of biosensors useful for identifying the presence of a bio-molecule in a sample, and more specifically to particles capable of directly binding a wide variety of bio-molecules without the use of hybridizing reagents.

BACKGROUND OF THE INVENTION

Without limiting the scope of the invention, its background is described in connection with methods to develop substrates that bind to biological molecules, as an example.

One example is a Membrane-based assay as disclosed in U.S. Pat. No. 7,407,768, which discloses a membrane-based assays using surface detector array devices suitable for use with a biosensor are disclosed. The device is formed of a substrate having a surface defining a plurality of distinct bilayer-compatible surface regions separated by one or more bilayer barrier regions. The bilayer-compatible surface regions carry on them, separated by an aqueous film, supported fluid bilayers. The bilayers may contain selected receptors or biomolecules. A bulk aqueous phase covers the bilayers on the substrate surface. Arrays may be engineered to display natural membrane materials in a native fluid bilayer configuration, permitting high-throughput discovery of drugs that target and affect membrane components. The membrane-based assays detect binding events by monitoring binding-induced changes in one or more physical properties of fluid bilayers.

U.S. Pat. No. 7,326,538 discloses compositions of mutated binding proteins containing thiol groups for coupling to sensor surfaces, analyte biosensor devices derived there from, and methods of their use as analyte biosensors both in vitro and in vivo.

It has been noted that "Microstructures generated from photostructurable glass have been already applied commercially for inkjet printer heads, electrodes for high quality head phones, micro-lens arrays, mechanical guiding structures, positioning devices, thermal exhaust control sensors, functionalized packaging structures for Microsystems, sterilizable filter plates and various other microstructure products." Furthermore, "Microsystem techniques serving diverse application areas, e.g. in sensors, microanalysis, actuating or micro-optics, have generated an increasing demand for glass and glass ceramic components with microstructures, in combination with high accuracy and narrow tolerances." It is also clear that "Microstructured glasses are used in flow, radiation, temperature and humidity sensors, and printing heads in ink jet printers are made with them. In the area of actuators they are enjoying increased usage as parts for microswitches, micropumps, valves and pressure heads, as well as implants in the medical field. Finally, photo sensitive glass and glass ceramics with their technological features and properties are now taken for granted and taking the lead from materials like silicon, plastics, ceramics and metals for certain applications."[1-7]

SUMMARY OF THE INVENTION

The present inventors have found that photosensitive glass can be processed to provide enhanced sensitivity for biological-testing. The enhanced binding and attachment is due to the formation of ceramic areas using metal nanoparticles created by the present invention. Moreover, areas of metal nanoparticles such as what the present inventors have been created using photosensitive glass created by other processes. Thus, the present invention is directed toward providing patterned areas of spaced-apart metal nanoparticles and the formation of patterned crystalline structures in glass-ceramics on substrates for biological-testing.

The present invention provides a method of forming one or more biological-binding areas on a substrate for biological-testing. The method includes activating at least a portion of a glass-ceramic substrate comprising glass and one or more metal containing compounds. The one or more metal containing compounds have a range of diameters that are less than about 300 nanometers in diameter and are spaced an average distance of at least one-half the midpoint of the diameter range apart. The one or more metal include compounds selected from metal oxides, metal nanoparticles, metal alloys, and atomic metals. The glass-ceramic substrate is heated to a temperature near the glass transformation temperature to form one or more metal nanoparticles in one or more ceramic biological-binding areas. The glass-ceramic substrate is etched to expose one or more metal. One or more biological molecules are contacted with one or more ceramic biological-binding areas to provide one or more biological testing areas with an increased binding area as compared to unactivated areas.

The present invention provides a patterned biological-binding substrate for biological-testing. The substrate includes a glass-ceramic substrate comprising one or more glass areas and one or more ceramic biological-binding areas comprising exposed metal nanoparticles, wherein at least half of the one or more metal nanoparticles are 1-500 nanometers in diameter and spaced from other metal particles by an average distance of at least 2 nanometers, wherein the one or more ceramic biological-binding areas provide greater binding than the one or more glass areas.

The one or more metal containing compounds are activated by exposing at least a portion of the glass substrate to an activating energy source. The glass substrate is metal-coalescing baked to a temperature above the glass transition temperature to form one or more ceramic biological-binding areas comprising one or more nanoparticles. The glass substrate is etched to expose the one or more metal nanoparticles from within the one or more ceramic biological-binding areas. One or more biological molecules are attached to the one or more ceramic biological-binding areas.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
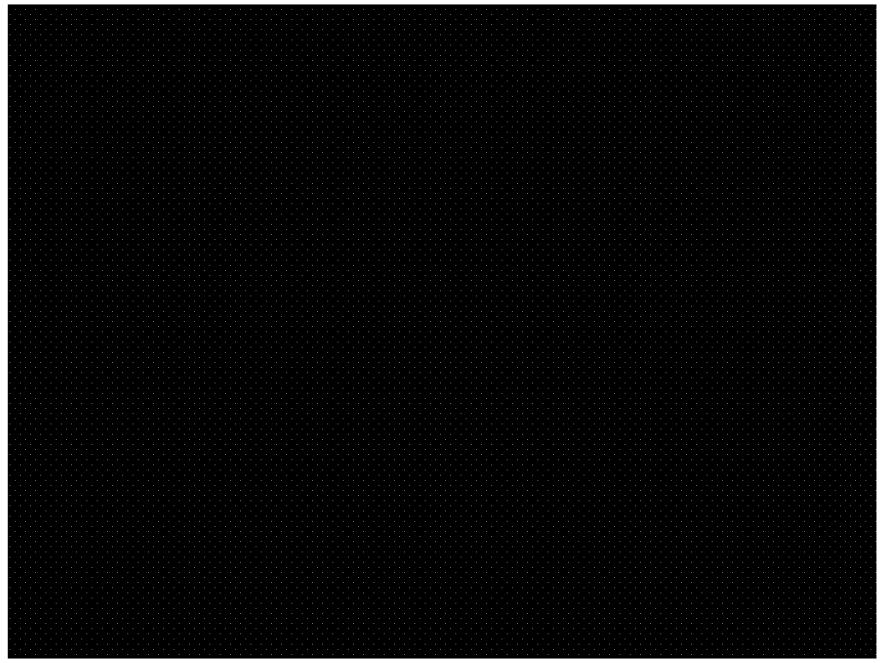
FIG. 1 is an image of a 26 gauge wire immobilized with Goat anti-rabbit antibody conjugated with phycoerythrin protein for fluorescent detection. The protein was incubated for 60 minutes with the wire and a 5 sec image was taken using a CCD camera. Despite the extended exposure, there was no detectable fluorescence.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. As used throughout this specification, percent (%) refers to weight percent.

As used herein, the term APEX binding glass is used to denote a composition as disclosed in U.S. application Ser. No. 12/058,608, and U.S. provisional Patent Application Ser. No. 60/968,325 both of which are incorporated herein by reference. Generally, the composition includes, by weight, of 71.66% silicon oxide ($SiO_2$), 0.75% boron oxide ($B_2O_3$), 0.4% antimony trioxide ($Sb_2O_3$), 11% lithium oxide ($Li_2O$), 6% aluminum oxide ($Al_2O_3$), 2% sodium oxide ($Na_2O$), 0.15% silver oxide ($Ag_2O$), and 0.04% cerium oxide ($CeO_2$) of by weight, and exposing one portion of the photosensitive glass substrate with ultraviolet light (305 nm to 315 nm) using an activation exposure of 9 $J/cm^2$, while leaving a second portion of said glass wafer unexposed. The binding substrate was heated to a temperature of 500° C. for one hour and then to a temperature of 600° C. for one hour and then cooled to transform at least part of the exposed glass to a crystalline material. The substrate was then etched in an HF-containing etchant solution.

As used herein, the term "substrate" denotes a variety of different substances including glass, polymeric materials, agent binding surfaces, plastics, other glasses, or other manufacturable materials.

The present invention provides a mechanism and substrate to allow biological molecules to attach to defined areas of ceramic, bounded by glass, formed by spaced-apart metal nanoparticles with a subsequent bake and etch step. Target molecules in solution, can attach to the bound biological molecules and, with a suitable fluorescent marker target molecules can be detected. For example, a number of possible capture-detection configurations are possible such as antigen-antibody, antibody-antigen, Sandwich ELISA, aptamers, enzyme-substrate, receptor-ligand, protein-drug, protein-liposome, and antibody-carbohydrate. While fluorescence detection methods are preferred method of detection due to its simple, safe, extremely sensitive nature and high resolution, other methods of detection are also possible such a rolling circle amplification, radioisotope labeling, surface-enhanced laser desorption/ionization (SELDI) mass spectrometry, atomic force microscopy, as well as surface plasmon resonance, planar waveguide, and electrochemical detection are all possible with these surfaces.

The present invention provides a method of forming one or more biological-binding areas on a substrate for biological-testing. The method includes activating at least a portion of a glass-ceramic substrate comprising glass and one or more metal containing compounds. The one or more metal containing compounds have a range of diameters that are less than about 300 nanometers in diameter and are spaced an average distance of at least one-half the midpoint of the diameter range apart. The one or more metal include compounds selected from metal oxides, metal nanoparticles, metal alloys, and atomic metals. The glass-ceramic substrate is heated to a temperature near the glass transformation temperature to form one or more metal nanoparticles in one or more ceramic biological-binding areas. The glass-ceramic substrate is etched to expose one or more metal. One or more biological molecules are contacted with one or more ceramic biological-binding areas to provide one or more biological testing areas with an increased binding area as compared to unactivated areas The patterning one or more discrete binding areas on the glass-ceramic substrate to form one or more metal nanoparticles within the one or more discrete binding areas may be accomplished in various ways known to the skilled artisan. For example, screen printing, photo lithography or a combination thereof may be used to form a pattern mask on at least a portion of the glass-ceramic substrate to protect at least a portion of the glass-ceramic substrate from activation to form one or more discrete binding areas. Similarly, screen printing photo lithography or a combination thereof may be used to form an etching pattern mask on at least a portion of the glass-ceramic substrate to protect at least a portion of the glass-ceramic substrate from etching to form one or more discrete binding areas.

The step of activating includes metal-precipitating one or more metal nanoparticles from metal oxides and the step of heating comprises metal-coalescing baking the glass-ceramic substrate. Although many different mechanisms may be used in the activation step, one common mechanism includes exposing at least a portion of a glass-ceramic substrate to an activating energy source. The one or more metal oxides are exposed to high-energy particles to reduce the one or more metal oxides to one or more metal nanoparticles.

The one or more metal nanoparticles are assayed by techniques using surface plasmon excitation, e.g., surface enhanced fluorescence (SEF), metal enhanced fluorescence (MEF), surface enhanced Raman scattering (SERS), surface plasmon resonance (SPR) or surface enhanced resonance Raman scattering (SERRS).

The one or more biological molecules attached to the one or more ceramic biological-binding areas may include one or more chromophores, one or more fluorophore, one or more luminescent compounds, one or more radioactive labels or a combination thereof; however, the composition that interacts with the one or more biological molecules may include a label. In another embodiment, both the one or more biological molecules and the contacting molecule may be labeled. The present invention may be used for biological-testing of one or more DNA, RNA, PNA, proteins, peptides, carbohydrates, lipids, ligands, enzymes, phage antibody-display, ribosome display, kinases, radioactive compositions, pro-drugs, drugs, receptors, hapten, pathogen, toxin, hormone, chemicals, liposomes, carbohydrate, organic compounds, compounds containing at least one non-binding electron pair, other biological compounds or combinations thereof.

The present invention provides a patterned biological-binding substrate for biological-testing having a glass-ceramic substrate comprising one or more glass areas and one or more ceramic biological-binding areas comprising exposed metal nanoparticles, wherein at least half of the one or more metal nanoparticles are 1-500 nanometers in diameter and spaced from other metal particles by an average distance of at least 2 nanometers, wherein the one or more ceramic biological-binding areas provide greater binding than the one or more glass areas.

The present invention shows a dramatically enhanced binding and attachment of biological molecules using defined areas of ceramic, bounded by glass, formed by the creation of spaced-apart metal nanoparticles with a subsequent bake and etch step, rather than surface areas of either metal or glass. It is well understood that the distortion of a biological molecule bound to surfaces can reduce the ability to bind target molecules. The present invention provides a surface which binds biological molecules and causes minimal, or zero, conformational distortion, to enable the bound biological molecule to more efficiently bind target molecules. The binding of the target molecule to the biological molecule may be detected using a variety of techniques, including fluorescent detection.

Preferably, the substrates are transparent or translucent to provide for convenient optical sensing, e.g. using fluorescent markers. In many preferred embodiments, photosensitive glass structures are used herein for the biological-binding surfaces (e.g. as a selected portion of a photosensitive glass substrate, using a thin photosensitive glass coating on a non-photosensitive substrate; or photosensitive glass microspheres deposited onto a non-photosensitive substrate). Photosensitive glass can provide an inexpensive and practical method of creating defined areas of ceramic, bounded by glass, formed by the creation of spaced-apart metal nanoparticles with a subsequent bake and etch step.

These metal nanoparticles can be comprised of metals with the ability to bind non-bound electron pairs present on various molecules in solution. These metals may consist of high-protein-affinity elements like silver, gold, platinum, rhodium, palladium, cerium, nickel, cobalt, copper, or their alloys or combinations of these metals or alloys. The substrate housing the metal nanoparticles may consist of glass, plastics, organic films (e.g. nitrocellulous, polystyrene, sol-gels, etc); and/or ceramics. In some embodiments, low-or-no-protein-affinity metals such as aluminum or zinc may be used for the substrate. Thus, the present invention uses metal nanoparticles in a lower-or-no-metal nanoparticle substrate. The present invention obtained dramatically improved binding results with such an arrangement. The present inventors believe that such spaced-apart metal nanoparticles greatly reduce biological molecule conformational distortion and thus greatly improve target molecule binding to biological molecules.

The present invention provides an inexpensive and rapid method for fabricating a pattern of biological binding areas for biological-testing, using defined areas of ceramic, bounded by glass, formed by the creation of spaced-apart metal nanoparticles with a subsequent bake and etch step, on a substrate. Biological molecules can be attached to ceramic through a variety of mechanisms, and the areas can provide a chemistry for increased biological binding as compared to unpatterned areas. The patterning may be fabricated using a variety of processes, such as exposing areas of a photosensitive glass substrate to create areas of metal nanoparticles via energy transfer, containing micro-particles or nanoparticles (e.g. of at least one of silver, gold, platinum, rhodium, palladium, cerium, nickel, cobalt, and copper, or their alloys or combinations of these metals or alloys) on/in a substrate.

Patterning of the areas may be accomplished by at least one process step selected from the group consisting of, exposing the material to an activating energy source (e.g. UV light to reduce a metal-oxide to metal), baking the material having a glass transition temperature at a temperature above said glass transition temperature (e.g. to allow metal atoms to coalesce into metal micro-or-nanoparticles), etching of areas to expose metal nanoparticles from within a substrate (e.g. where the metal micro-or-nanoparticles are etched slowly, if at all, compared to other material in the substrate, e.g. silver particles in a glass substrate etched with HF to increase the surface area and the exposure or near-exposure of metal particles); and depositing patterned areas of biological-binding-glass (e.g. thermal evaporation or micro-spheres containing metal micro-or-nanoparticles) on a substrate.

The present invention includes a method of providing a pattern of biological-binding areas for biological-testing, comprising: the creation of areas for metal nanoparticles on a substrate; patterning the selected areas by at least one process step selected from the group consisting of, exposing the areas of the material to an activating energy source (e.g. to reduce metal-oxide to a metal), baking a material at a temperature above the glass transition temperature (to coalesce reduced metal), etching the areas to expose metal nanoparticles from within the areas; and depositing patterned areas of biological-binding-glass on a substrate (to directly pattern the area, e.g. thermal evaporation or with nanoparticle containing microspheres); and attaching biological molecules to the selected areas (to provide binding sites for target molecules), such that the areas provide a chemistry for increased binding as compared to unselected areas. The metal particles may have a range of diameters; for example, with midpoint of the diameter range of less than about 300 nanometers in diameter. In addition, metal particles may be spaced from other metal particles by an average distance of at least one-half the midpoint of the diameter range. As noted above the present invention has shown a greatly enhanced sensitivity using defined areas of ceramic, bounded by glass, formed by the creation of spaced-apart metal nanoparticles with a subsequent bake and etch step.

Thus, the present invention provides a method for fabricating discrete patterns of biological-binding areas within areas which minimizes or exclude biological molecule binding depending on the initial biomolecule concentration used to coat the surface. The patterned biological-binding areas greatly enhanced biological molecule binding by fabricating areas which contain metal nanoparticles on and within a substrate. Biological molecules attached to the defined areas of ceramic, bounded by glass, formed by spaced-apart metal nanoparticles with a subsequent bake and etch step, which provide a chemistry for increased biological molecule binding.

The present invention includes distinct binding and non-binding regions of any shape and size, from 310 nm up to any desired size. In addition, the present invention may be used for SEF, SERS, SPR, SEERS. In addition, the imbedded nanoparticles of the present invention may be translated into other materials such as sol-gels, zeolites, hydrogels, and other glass or product formulations. The skilled artisan will recognize that common deposition techniques may be used in the present invention, e.g., CVD, electron beam, and so forth. In addition, the particles may be incorporated into common chromatography devices, such as microarrays, microfluidic channels, and chromatography columns.

The present invention provides a method for fabricating discrete patterns of biological-binding areas within areas which minimize biological molecule binding. The patterned biological-binding areas demonstrate greatly enhanced biological molecule binding by fabricating areas which contain metal nanoparticles on and within a substrate. Biological molecules can be either attached to the metal nanoparticles in these areas, and/or adsorped/absorbed in these areas through known molecular forces such as ionic bonds, hydrogen bonds, simple adsorption, and hydrophobic interactions with the surface. This provides a surface chemistry for increased biological molecule binding. Further information regarding surface-enhanced fluorescence technology is given in the references cited below. Again, the use of a photosensitive glass can provide an inexpensive and rapid method for such fabrication. Creating the metal nanoparticles from within a glass (or ceramic) avoids the problems of handling nanoparticles of metal.

FIG. 1 is a picture of a 26 gauge wire immobilized with Goat anti-rabbit antibody conjugated with phycoerythrin protein for fluorescent detection. The protein was incubated for 60 minutes with the wire and a 5 sec image was taken using a CCD camera. Despite the extended exposure, there was no detectable fluorescence.

The present invention provides that surfaces which contain spaced-apart metal nanoparticles in a glass substrate provides greatly enhanced biological molecule binding, as compared to identical immobilization protocols conducted on 99.99% pure silver wire surfaces. The silver metal wire showed very little (essentially none, even with a longer exposure, see below) fluorescence as detected with a CCD camera using a 5 second exposure. In contrast, the present invention's material containing discrete areas with spaced-apart metal nanoparticles in a glass substrate fluoresced substantially more than the silver wire over the entire surface, as detected with a CCD camera using a 1 second exposure. Silver has been used for binding non-binding pairs of electrons present in amino acids found in proteins and peptides.

Figure 2:
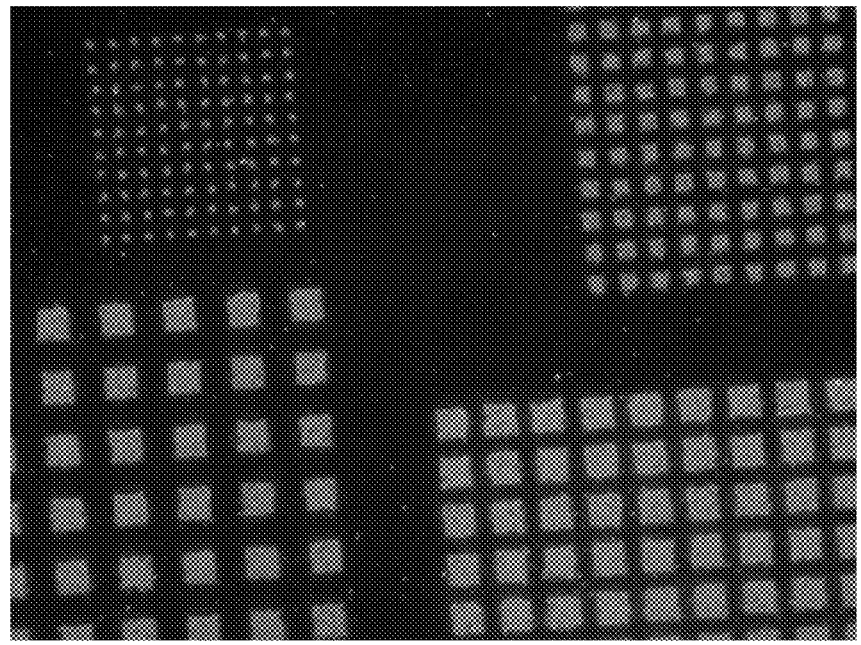
FIG. 2 is an image of an APEX™ based array which was immobilized with Goat anti-rabbit antibody conjugated with phycoerythrin protein for fluorescent detection. The protein was incubated for 60 minutes with the glass and a 1 sec image was taken using a CCD camera.

FIG. 2 is a picture of an APEX™ based array which was immobilized with Goat anti-rabbit antibody conjugated with phycoerythrin protein for fluorescent detection. The protein was incubated for 60 minutes with the glass and a 1 second image was taken using a CCD camera.

The present inventors discovered that the formation of ceramic by the induction of spaced-apart metal nanoparticles provide more adequate binding sites for the binding of biological molecules through a variety of mechanisms including hydrogen binding and binding to the metal nanoparticles with much less distortion, and that reduced distortion of the biological molecules increases their ability to bind target molecules.

The metal nanoparticles can be comprised of metals with the ability to bind non-bound electron pairs from molecules in solutions. These metals can consist of, but not limited to, high-protein (or other biological molecule)-affinity silver, gold, platinum, rhodium, cerium, nickel, cobalt, copper, or their alloys or combinations of these metals or alloys. These metals and their alloys may be referred to herein, as metal nanoparticles. The substrate containing the metal nanoparticles may consist of glass, plastics, organic films, such as nitrocellulous, polystyrene, sol-gels, and/or ceramics. In some embodiments low-or-no-protein-affinity metals such as aluminum or zinc may be used for the substrate. Thus the present invention uses metal nanoparticles in a lower (or-no) biological-molecule-binding substrate. The present inventors have obtained dramatically improved binding results with such an arrangement. It is believed that regions that posses spaced-apart metal nanoparticles bind more biological molecules and greatly reduce biological molecule conformational distortion and thus greatly improves target molecule binding to biological molecule.

Preferably, the metal nanoparticles are at least one of silver, gold, platinum, rhodium, palladium, nickel, cobalt, copper, or their alloys or combinations of these metals or alloys. In some embodiments, the biological-binding-areas are of a glass containing oxide of at least one of silver, gold, and copper, and wherein at least some of the oxide of at least one of silver, gold, and copper is reduced to metal with an activating energy source to provide the basis of ceramic formation. In some embodiments, the metal particles that are exposed from within the glass are formed by metal-precipitating and then metal-coalescing baking. In some embodiments, the areas are exposed and patterned using high-energy particles (including UV light) to reduce at least some of the oxide of at least one of silver, gold, and copper in the areas to metal.

Photoetchable glasses have been found to have several advantages for the fabrication of a wide variety of Microsystems components. Microstructures may be produced relatively inexpensively with these glasses using conventional semiconductor processing equipment. These glasses are transparent in 400-1200 nm, possess high temperature stability, good mechanical properties, are electrically insulating, and have better chemical resistant than plastics and many metals to acids, bases, oxidizers, and solvents.

The present invention uses several inorganic binding mechanisms for binding. For example, the particles of the present invention include silver nanoparticles that contribute to a coordinated covalent binding of free thiols (cysteine) and amines (histidine). Still other interactions include the hydrogen binding with free (OH— and COOH— moieties). In addition, the silver-fluoride dipole can aid in the biomolecule binding. Given the nature of the material, ionic interactions between the biomolecules and the glass are also available. The skilled artisan will recognize the present invention may be used to bind target molecules, other molecules and/or complexes, e.g., DNA, RNA, PNA, proteins, peptides, carbohydrates, lipids, ligands, enzymes, phage antibody-display, ribosome display, kinases, radioactive compositions, prodrugs, drugs, receptors, hapten, pathogen, toxin, hormone, chemicals, liposomes, carbohydrate, organic compounds, compounds containing at least one non-binding electron pair, other biological compounds or combinations thereof.

Although, the examples above are biomolecules, the present invention is not limited to biomolecules. The present invention may be used to bind organic molecules, viruses, hydrocarbons, aromatic compounds, aliphatic compounds, drugs, inorganic compositions and composites and similar compositions.

In many embodiments, the substrates are translucent, preferably transparent. Transparency facilitates visual or other electromagnetic detection methods. The use of a photosensitive glass-ceramic either as a substrate, or as a coating on a substrate, or as a patterned coating on a substrate, or as microspheres on a substrate, can provide an inexpensive and rapid method for such fabrication. In the use of a photosensitive glass either as a substrate, or as a coating on a substrate a pattern for creating spaced-apart metal nanoparticles can be determined by exposing some areas (e.g. by light or other high-energy particles) to nucleate nanoparticles (by further processing) for ceramic formation for binding biological molecules, while unexposed photosensitive glass areas will have substantially no metal nanoparticles and will create ceramic (by further processing) and not bind biological molecules.

Although not wanting to be bound by theory, the present invention's binding mechanism may be one of more of the following. Biological molecules bind to surfaces through many different mechanisms.

For example, the metal nanoparticles directly bind several amino acid-containing molecules, such as proteins and peptides, in a coordinated-covalent bond; where D-orbitals of the metal nanoparticle bind free non-binding electrons on the biological molecule. A variety of amino acid side groups bind to the noble metal nanoparticles in this manner. Proteins are composed of 20 main amino acids. These amino acids have various side groups that contain compounds that can bind to noble metal nanoparticles in this manner. Examples of some amino acids which may directly bind to the noble metal nanoparticles include: arginine, asparagine, cysteine, glutamine, histadine, and lysine. Therefore, thiol-groups in cysteine, amine groups in lysine, free heterocyclic aromatics (imidazole side chain) on histidine, and other capable moieties interact with the D-orbitals of the silver (noble metals or copper) nanoparticles forming a coordinated-covalent bond. This bond possesses a high bond energy, 51.9 kcal/mol for silver-thiol bonds, causing a nearly non-reversible binding event with the biomolecule. Likewise, the noble metal nanoparticles bind nucleic acid molecules by binding the N7 position of guanine nucleotides found in nucleic acid-based molecules, such as DNA and RNA.

Biological molecules bind to surfaces through hydrophobic interactions within the glass, hydrogen binding with free ($OH^-$ and $COOH^-$ moieties) and adsorption onto compounds present within the crystallized glass that are hydrophobic or hydrophilic.

Biological molecules also bind to surfaces during the etch process as fluoride ions from hydrofluoric acid remove silicon dioxide in the glass substrate, silver nanoparticles become exposed to the solution and fluoride ions bind to the silver nanoparticle; fluoride ions (i.e., Lewis base) may act as chemical ligands forming coordinated covalent bonds with metal cations (i.e., Lewis acid). This polar silver fluoride compound binds biomolecules through charged interactions.

Also, Biological molecules bind to surfaces through cerium binding the proteins and lithium aluminum hydroxide produced during the processing of the glass. Lithium aluminum hydroxide is a powerful reducing agent in organic chemistry. The material may convert all $NH^{3+}$ side groups into $NH_2$, capable of binding to nanoparticles, at a lower pH. Proteins like to be immobilized at their isoelectric point, which varies a lot from protein to protein. Therefore, the pH at which a protein is immobilized is very important in traditional immobilization chemistries. By making sure all amines are in the $NH_2$ configuration, we could expand the range at which proteins are immobilized under "neutral" conditions.

In addition to the native binding mechanisms present above, the surface of the entire material, or pre-defined and processed portions of the material, may be modified in a variety of manners. It is a still further object of this invention to provide several methods for preparing biological binding sites for coupling by covalent attachments to analytes by creating additional functional groups from the available hydroxyl groups within the glass. These groups include carboxylates, esters, alcohols, carbamides, aldehydes, amines, sulfur oxides, nitrogen oxide, halides, epoxy, avidin, strepavidin, or nitrosylated polysaccharide. These groups are known to facilitate attachments of analytical reactants. In addition, all the known silane chemistries maybe applied to the surface glass which contains numerous hydroxyl groups created within the patterned biologic binding area. However, all forms of analyte attachments, such as ionic bonds, hydrogen bonds, simple adsorption as well as hydrophobic interactions with the surface are available.

The metal nanoparticles can be of high-biological molecule-affinity silver, gold, platinum, rhodium, palladium, cerium, nickel, cobalt, copper, or their alloys or combinations of these metals or alloys, or oxides of these elements. The substrates (e.g., glasses, glass-ceramic substrates, substrates, etc) can include glass, plastics, nitrocellulous, polystyrene, sol-gels, glass-ceramics, and/or ceramics, and in some embodiments even low-or-no-protein-affinity metals such as aluminum or zinc may be included for the substrate. For example, for proteins we use high-protein-affinity metal nanoparticles in a low-or-no-protein-affinity substrate. In some cases, we may have metal nanoparticles within a substrate of glass or ceramic, which is in turn within a substrate of, e.g., plastic.

In some embodiments, traditional materials used for biological molecule binding, such as polystyrene and nitrocellulous membranes, are imbedding with higher affinity metal nanoparticles. These nanoparticles are used to bind a greater number of biological molecules in a manner which causes reduced molecular distortion and may be used for SEF, SERS, SPR, SEERS. For example, in materials which are spin coated onto surfaces for biological molecule binding, such as nitrocellulous and other organic membranes, metal nanoparticles may be included in the actual material which is spun onto the surface. Metal or metal-containing material may be patterned while being deposited (e.g. sputtered through a metal mask), or deposited and then patterned (e.g. using patterned photoresist for an etching resist or a rejection mask).

Likewise, in materials which are not spin coated onto surfaces but are instead bulk materials, such as glasses and plastics, metal nanoparticles may be imbedded into the bulk material through a variety of mechanisms, such as ion implantation, inclusion of metal nanoparticles into the original melt, or other known methods of nanoparticle implantation. Ion implantation may also be used on a surface and may again be patterned during or after being deposited. Nanoparticles may be included by processing a photo-sensitive glass, e.g. by our melt compositions, with at least one of the following processing steps: exposure, baking, etching. The addition of iron complexes may be used to make the material magnetic. In addition, other ingredients such as barium oxide or lead oxide may be added to increase the index of refraction to increase brightness.

In some embodiments, the creating of a pattern of biological-binding-areas is done by screen printing glass microspheres containing oxide of at least one of silver, gold, and copper, and wherein at least some of the oxide of at least one of silver, gold, and copper is reduced to metal to provide the metal particles, surface-activating etching of the microspheres, and wherein the screen printing is done on a substrate without biological-binding areas. In some embodiments, the creating of a pattern of areas of biological-binding is done by screen printing glass micro-grains containing micro-particles or nanoparticles of at least one of silver, gold, platinum, rhodium, palladium, nickel, cobalt, copper, or their alloys or combinations of these metals or alloys.

In some embodiments, the metal particles are added as pure metal, or metal alloy, particles during fabrication of the biological-binding-material, rather than the currently generally preferred method of being reduced from an oxide or a salt in a glass. In some embodiments, the metal particles are added as metal salt during fabrication of biological-binding-glass. Further, in some embodiments, the substrate containing the metal particles is a non-glass (although still preferably transparent or translucent). Generally, the low-or-no-biological-molecule-binding substrate can be of glass, plastics, silicon, germanium, organic films, such as nitrocellulous, polystyrene, sol-gels, and/or ceramics, or even low-or-no-biological-molecule-binding metals such as aluminum or zinc.

In some embodiments, metal particles are added as particles through energetic deposition through such techniques as CVD, plasma deposition, ion implantation, and other methods known to the skilled artisan.

Also, metal nanoparticles-containing coatings can also be patterned (e.g. by etching or by screen-printing, ink-jet printing, or other printing method) to provide a pattern of biological-binding areas. The pattern may be very fine on a very small substrate and thus the biological testing may be done in vivo as well as in vitro.

The present invention can also be a method of providing a pattern of biological-binding areas for biological-testing, by selecting areas for the creation of metal nanoparticles on a substrate; patterning the selected areas by at least one process step selected from the group consisting of, exposing the material to an activating energy source to activate metal particles, baking a material having a glass transition temperature at a temperature above the glass transition temperature to activate metal particles, etching the areas to expose metal particles from within the glass; and depositing patterned areas of biological-binding-glass or biological-binding-organic on a substrate; and attaching biological molecules to the selected areas.

In some embodiments, the biological-binding-organic contains at least one non-binding electron pair, or uses ionic bonds, hydrophobic, hydrophilic, van der Waals forces, and hydrogen bonds to bind to the surface. In some embodiments, the metal particles are used for assay techniques which incorporate plasmon excitation of proximal noble metal clusters, and the metal particles used for, but not limited to, surface enhanced fluorescence (SEF), surface enhanced Raman scattering (SERS), and surface plasmon resonance (SPR).

In some embodiments, the biological-testing includes testing of at least one of DNA, RNA, proteins, peptides, and other amino acid containing molecules. In addition, testing may include the use of carbohydrates, lipids, ligands, kinases, and other biological compounds.

The present invention can also be a method of providing a pattern of biological-binding areas for biological-testing by selecting areas for metal particles on a substrate; patterning the selected areas by at least one process step selected from the group consisting of; exposing the area to an activating energy source, baking the material having a glass transition temperature at a temperature above the glass transition temperature, etching the areas to expose portions of metal particles or nearly expose metal particles from within a solid; and depositing patterned areas of biological-binding solid on a substrate; and attaching biological molecule to the selected areas.

In some embodiments, a surface-smoothing acid of nitric acid is used to dissolve surface metallic silver, and/or hydrochloric acid to dissolve surface cerium metal, is used during or after the HF etch, (if both acids are used, they may be used separately, or together) whereby surface roughness of at least one micro-optic device in the shaped glass structure is reduced and whereby light transmission through surfaces of a micro-optic device is increased, and light scatter is decreased. Additionally, some embodiments may require the use of a buffered HF etch solution.

The glass structure may be patterned to create exposed regions of higher index of refraction surrounded by areas of lower index of refraction, such that light is substantially contained within the higher index of refraction material. Conversely, the patterned glass structure may be patterned to create exposed regions of higher index of refraction surrounding areas of lower index of refraction, such that light is substantially contained within the lower index of refraction material. Either way, exposing the glass of the present invention with such ultraviolet light can raise index of refraction of the glass and the changed index of refraction may be used to direct, manipulate, or process photons. Thus, altering index of refraction may be used to direct light more efficiently to and/or from a particular area within a pattern of biological-binding areas.

In some embodiments, the glass structure is heated to above its glass transition temperature for between 10 minutes and 12 hours and then heated above its glass-ceramic transition temperature (at least 10° C. above its glass transition temperature) for between 10 minutes and 12 hours. It will be understood, that the time may be for any duration between 10 minutes and 12 hours and that the temperature may be any temperature above 10° C.

In some embodiments, the patterned glass structure is heated to above its glass transition temperature for between 10 minutes and 12 hours to allow the metals to coalesce and act as nuclei for devitrification in the exposed portion of the photosensitive glass substrate, and then the glass substrate is heated above its glass-ceramic transition temperature (at least 10° C. above its glass transition temperature) for between 10 minutes and 12 hours. This provides for transformation of the exposed portion of the photosensitive glass substrate into a glass-ceramic during a subsequent cooling of the glass substrate. The glass substrate can then be etched in an HF-containing etchant solution, to expose more of the metal (or one or more metal nanoparticles) and/or to give an etch ratio of exposed-portion to unexposed-portion of at least 5:1 in a shaped glass structure. Such an etch may be used to direct light more efficiently to and/or from a particular area within a pattern of biological-binding areas.

The glass substrate may also be heated to a temperature in excess of the glass transformation temperature to allow at least part of the reduced noble metal to coalesce to provide a patterned glass structure is used to form larger clusters for at least one plasmon analytical technique, e.g. surface enhanced fluorescence, surface enhanced Raman spectroscopy, and surface plasmon resonance. The exposure wavelength may be varied from 300-320 nm and be of any wavelength necessary and range from 200-900 nm.

Preferably, all photosensitive glass embodiments are essentially germanium-free. In some embodiments, $Sb_2O_3$ is added (e.g. at least 0.01% $Sb_2O_3$) to help control the oxidation state of the composition. In some embodiments, at least 0.85% $B_2O_3$ is included, and in other embodiments at least 1.25% $B_2O_3$ is included. In some preferred embodiments, at least 0.001% $Au_2O$ is included in addition to at least 0.15% $Ag_2O$. In some embodiments, a combination of CaO and/or ZnO is added up to 18%. In some embodiments, up to 10% MgO is added. In some embodiments, up to 18% lead oxide is added. Up to 5%, $Fe_3O_4$, may be added to make the material magnetic. The preferred wavelength of the ultraviolet light used for exposure is about 308-312 nm, however other wavelengths may be used. In making the glass of the present invention, salts can be used as ingredients rather than oxides.

In some embodiments, photosensitive glass may have a composition comprising; less than 72% silica, at least 0.15% $Ag_2O$, at least 0.75% $B_2O_3$, at least 11% $Li_2O$, and at least 0.0014% $CeO_2$; exposing at least one portion of the photosensitive glass substrate with ultraviolet light 240 to 360 (in some embodiments, 300-320, 240-320, 200-360, 200-400) nm light or a directed source of protons using an activation exposure of 0.8-15 $J/cm^2$, while leaving at least a second portion of the glass wafer unexposed; heating the glass substrate to a temperature of 550-650° C., and holding the glass substrate for at least ten minutes at a temperature of 550-650° C. (e.g. to coalesce metal into metal particles). The skilled artisan will recognize that other temperatures (e.g., 400-800° C.) may be used and other durations. In some embodiments, the method uses a photosensitive glass substrate that is not limited to the above composition or processing parameters.

In some embodiments, unetched biological-binding areas are used. Etching is used in other embodiments to remove glass to expose more surface area of nanoparticles. Etching can also, for example, expose more surface area for biomolecule binding on a glass slide and/or direct light more efficiently to and/or from a particular area within a pattern of biological-binding areas.

The present invention uses a glass of the above type and showed a surprising sensitivity to ultraviolet light exposure of over three times that of the commercially available photosensitive glass. The difference between the glass of the present invention and the commercially available photosensitive glass are also shown by improvement in the etch rate (a surprising over six times faster etch rate) and improved etch ratio (the glass of the present invention had etch ratios of exposed portions to that of the unexposed portion of at least 40:1 to 50:1, while the best reported etch ratios of the commercially available photosensitive glasses are 30:1 or less). One reason might be that the lower exposure leads to less light scattering into the side walls, and thus less etching of the side walls. The preferred composition modifications of adding boron oxide and reducing the silica content (possibly decreasing the glass's susceptibility to etching with HF acid) might be leading to boron silicate formation that enhances crystallization, but in any case, these etching results are surprising. Again, such an etching can, for example, expose more surface area on a glass slide and/or direct light more efficiently to and/or from a particular area within a pattern of biological-binding areas.

Figure 3:
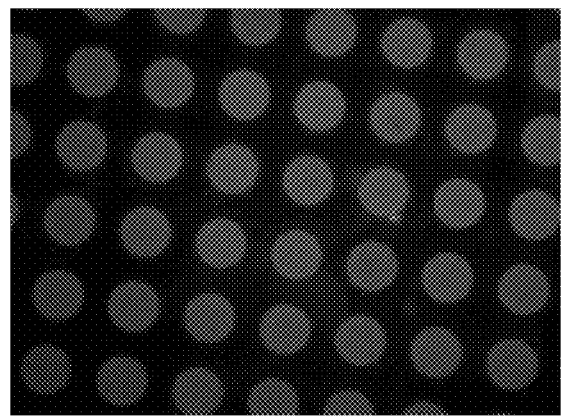
FIG. 3 is an image of areas of discrete biological binding of phycoerythrin-conjugated goat IgG antibody created on the photoetchable glass of the present invention.

FIG. 3 is a picture of areas of discrete biological binding of phycoerythrin-conjugated goat IgG antibody created on the photoetchable glass of the present invention.

Figure 4:
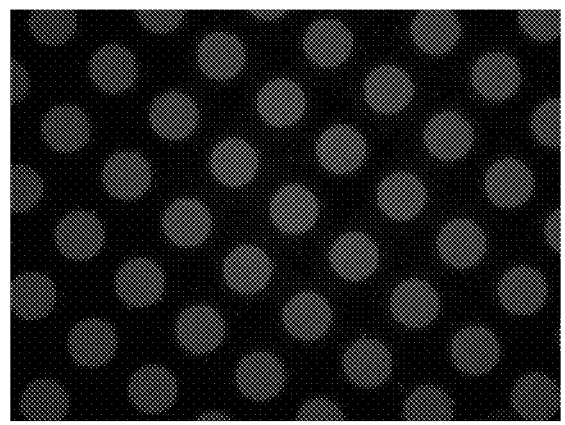
FIG. 4 is an image of areas of patterned biological binding of phycoerythrin-conjugated goat IgG antibody after incubation in 20% powdered milk for 6 hours.

FIG. 4 is a picture of areas of patterned biological binding of phycoerythrin-conjugated goat IgG antibody after incubation in 20% powdered milk for 6 hours. The areas of discrete biological binding were created on the photoetchable glass using the following parameters: 1) UV exposure, 2) bake, and 3) HF acid etch. The patterned surface was then flood coated with phycoerythrin-conjugated goat IgG for 1 hour followed by three rinses in phosphate buffered saline. The surface was then imaged at 50 milliseconds using fluorescence microscopy. The surface was then immersed in 20% powdered milk in PBS buffer for six hours at which time it was rinsed in PBS buffer and re-imaged at 50 milliseconds using fluorescence microscopy. It should be noted that almost no fluorescence signal is lost during this time at high milk protein concentration. This remarkable finding indicates that once the protein is bound to the surface, it is not easily detached and the avidity of the surface is great. Furthermore, it should be noted that the flood immobilization of the phycoerythrin-conjugated goat IgG antibody was localized to the patterned area and minimal binding occurred between the patterned areas.

Even more surprising and unexpected is the dramatically enhanced biological molecule binding achieved in processed areas over non-processed areas. Essentially, non-processed areas demonstrate minimal to absent binding of biological molecules when the proteins are flooded onto the fabricated surface (patterned and non-patterned regions alike). Another surprising find is that once the biological molecule is bound it essentially does not come off the surface, meaning that the avidity of the surface is extremely high. For example, phycoerythrin conjugated antibody coated onto areas of processing was not removed in the presence of 20% powdered milk. Typical concentrations of powdered milk solutions are approximately 4%. The phycoerythrin conjugated antibody remained bound for at least 6 hours in the presence of very high concentrations of protein found within the powdered milk. This is a much increased binding affect than observed over biological molecule binding to similar pure (macro-scale) metal. Again, the reason for the greatly enhanced fluorescence signal of bound biological molecules is unclear, but we believe that regions that posses spaced-apart metal nanoparticles (1) provide more compatible spaces for biological molecules to bind to and (2) enable binding of biological molecules to the metal nanoparticles with much less distortion than when the biological molecules are attached to a pure (macro-scale) metal surface; this distortion of the biological molecules reduces their ability to bind target molecules.

In addition, the present invention provides a method for preparing biological binding sites for using multiple compounds within the same patterned site. For example, by labeling two different proteins with an individual fluorochrome, such as rhodamine on one protein and fluorescein isothiocyanate (FITC) on the other, the two proteins could be captured on the same pattered area by separate antibodies for each protein within the same patterned area. Then detection analysis of both proteins could be performed by collecting emitted light from each fluorochrome. Another example would be where a protein from a disease sample is labeled with FITC fluorochrome and the identical protein from the control sample being labeled with rhodamine could be captured at the same time by the same patterned site with a single antibody and a ratio of the fluorescence intensity of the two fluorochromes could indicate changes in the disease state of the protein.

The present inventors have found that surfaces which incorporate spaced-apart metal nanoparticles (generally in a glass substrate), rather than surfaces of pure (macro-scale) silver metal (i.e. 20 gauge wire), provides greatly enhanced biological molecule binding. In one embodiment, a few scattered fluorescing spots were imaged using a CCD camera during a 5 second exposure of the surface of a metal wire. In contrast, substantially brighter fluorescence was observed over the entire surface of material containing spaced-apart metal nanoparticles (as detected with a CCD camera during only a 1 second exposure). The present inventors believe that the ceramic created by the spaced-apart metal nanoparticles provide more adequate binding sites for the binding of biological molecules through a variety of mechanisms to the ceramic with minimal to much less distortion, and that the reduced distortion of the biological molecules increases their ability to bind target molecules.

Figure 5:
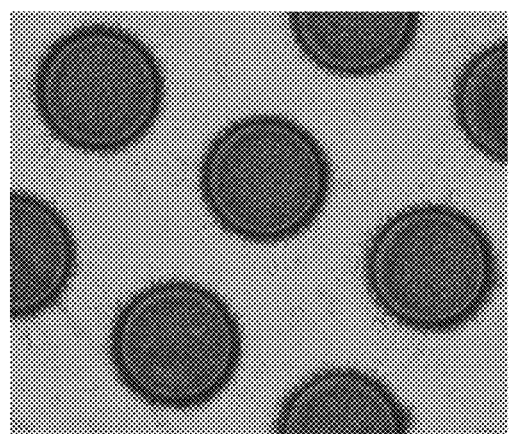
FIG. 5 is an image illustrating the increase in the surface are of the ceramic biological-binding areas of the present invention.

FIG. 5 is an image illustrating the increase in the surface are of the ceramic biological-binding areas of the present invention. Generally, the increase in the surface area provides additional sites for binding and interaction of various substrates. For example, the enhanced surface area offers more readily available areas that can be used in the formation of silane chemistries that facilitate the immobilization of biological molecules.

The patterning of biological-binding areas for greatly enhanced biological molecule immobilization and detection may be accomplished using a photosensitive glass. With this glass areas which contain metal nanoparticles may be fabricated to control the areas which bind large amounts of biological molecules and which areas bind lower amounts. Additionally, photosensitive glass particles can be deposited on a substrate, through a variety of techniques, such as sol-gel processing, spin coating, thermal evaporation, etc., either in a pattern layer or an unpatterned layer. The glass particles may exist in a variety of form factors such as microspheres, thin films, microfibers, etc.

The method of providing a pattern of biological-binding areas for biological-testing, may include: Patterning areas for the creation of metal nanoparticles on a substrate and patterning the areas by at least one process step selected from the group consisting of, exposing the areas to an activating energy source, baking a glass at a temperature above the glass transition temperature, etching the areas to expose metal nanoparticles from within the areas; and depositing patterned areas of biological-binding-glass on a substrate; and attaching biological molecules to the selected areas, such that the areas provide a chemistry for increased binding as compared to unselected areas. The metal nanoparticles may have a range of diameters (e.g. with midpoint of the diameter range of less than about 300 nanometers in diameter) and may be spaced from other metal particles, e.g. by an average distance of at least one-half the midpoint of the diameter range.

The metal nanoparticles may be at least one of silver, gold, platinum, rhodium, palladium, nickel, cobalt, copper, or their alloys or combinations of these metals or alloys. In some embodiments, the biological-binding-areas are of a glass containing oxide of at least one of silver, gold, and copper, and wherein at least some of the oxide of at least one of silver, gold, and copper is reduced to metal to provide the metal nanoparticles. In some embodiments, the metal particles that are exposed from within the glass are formed by metal-precipitating and then metal-coalescing baking. In some embodiments, the areas are exposed by patterned high-energy particles (including UV light) to reduce at least some of the oxide of at least one of silver, gold, and copper in the areas to metal.

In some embodiments, the creating of a pattern of biological-binding-areas is done by screen printing glass (or ceramic) micro-spheres (or micro-grains) containing oxide of at least one of silver, gold, and copper, and wherein at least some of the oxide of at least one of silver, gold, and copper is reduced to metal to provide the metal particles, and wherein the screen printing is done on a substrate prior to a surface-activating etching. In some embodiments, the creating of a pattern of areas of biological-binding is done by screen printing micro-grains containing nanoparticles of at least one of silver, gold, platinum, rhodium, palladium, cerium, nickel, cobalt, and copper, or their alloys or combinations of these metals or alloys. Note that the "glass" as referred to herein, may be at least partially crystallized. Further, rather than (or in addition to) oxides, it may contain nitrides, carbides, borides, and salts. Thus, as used herein, the term "glass" includes ceramics.

In some embodiments, at least one metal-coalescing baking step is done on glass micro-spheres, prior to screen printing of the glass micro-spheres on a substrate (e.g. with a sol-gel binder). In some embodiments, a surface activation etching after deposition on the substrate (alternatively in some cases, it is not used, and in still other cases it is used prior to deposition). In some embodiments, the metal particles are added as metal particles during fabrication of the biological-binding-material, rather than the currently generally preferred method of being reduced from an oxide or a salt. In some embodiments, the metal particles are added as metal salt during fabrication of biological-binding-glass. Further, in some embodiments, the substrate containing the metal particles is a non-glass (although still preferably transparent or translucent). In some embodiments, the micro-spheres are between 1 and 1,000,000 nanometers in diameter. In some embodiments, the metal particles are between 1 and 300 nanometers in diameter. In some embodiments, at least half the metal particles are 1-500 nanometers in diameter and spaced from other metal particles by an average distance of at least 2 nanometers. In some embodiments, at least half the metal particles are 1-500 nanometers in diameter and spaced from other metal particles by an average distance of at least 20 nanometers.

In some embodiments, the present invention uses photosensitive glass to create metal nanoparticles. As described below, metal oxides (e.g. silver) may be selectively reduced from the glass and coalesced into nanoparticles. In some embodiments, the initial glass composition may be (in weight percent): 65-72% silica, at least 3% $K_2O$ with 6%-16% of a combination of $K_2O$ and $Na_2O$, 0.15-5% of at least one oxide selected from the group consisting of $Ag_2O$ and $Au_2O$, 0.75%-7% $B_2O_3$, and 6-7% $Al_2O_3$, with the combination of $B_2O_3$ and $Al_2O_3$ not exceeding 13%, 8-13% $Li_2O$, and 0.014-0.1% $CeO_2$. In some embodiments, the composition is: 35-72% silica, 3-16% $K_2O$, 0.15-5% $Ag_2O$, 0.75-13% $B_2O_3$, 8-13% $Li_2O$, and 0.014-0.1% $CeO_2$. In some embodiments, the composition is 46-72% silica, 3-16% $K_2O$, 0.15-5% $Ag_2O$, 0.75-13% $B_2O_3$, 6-7% $Al_2O_3$, 11-13% $Li_2O$, and 0.014-0.1% $CeO_2$. Preferably in the above embodiments the $CeO_2$ is in the 0.04-0.1% range. In some embodiments, the glass substrate is heated to a temperature of 450-550° C. for between 10 minutes and 2 hours (e.g. 1 hour) and then heated to a temperature range heated to 550-650° C. for between 10 minutes and 2 hours (e.g. 1 hour). Note the heat treatment tends to crystallize the photosensitive glass, and that the "glass" as referred to herein, may be at least partially crystallized.

As noted above, the present inventors have now found that photosensitive glass can be processed to provide enhanced binding and attachment for biological-testing as compared to conventional surface areas of metal (e.g. areas of silver wire). However, the photosensitive glass may also be exposed and etched to direct light within photosensitive glass substrate, e.g. on the backside of a structure of patterned nanoparticles for directing interrogation light and/or directing fluorescence from a patterned biological-binding area. Thus the photosensitive glass may be used for both patterned nanoparticles and high precision etched structures. Kravitz et al. U.S. Pat. No. 7,132,054, noted above, suggests etching photosensitive glass as an inexpensive method of fabricating high precision microneedles, using a negative mold of FOTURAN photosensitive glass. The present invention's glass composition is referred to herein as "APEX glass" or simply "APEX" and can be similarly etched with even higher high precision. Such an approach can be improved by using APEX. A similar process exposure and etched can be used with our glass composition, and Kravitz et al's U.S. Pat. No. 7,132,054 is hereby incorporated by reference.

Thus, in the past, photosensitive glass has sometimes been used to create glass structures. Apparently the only currently commercially available photosensitive glass is FOTURAN, made by the Schott Corporation and imported into the U.S. only by Invenios Inc. FOTURAN comprises a lithium-aluminum-silicate glass containing traces of silver ions. When exposed to UV-light within the absorption band of the metal ion dopants in the glass, they act as sensitizer, absorbing a photon and stripping an electron that reduces neighboring silver ions to form colloidal silver atoms. These silver colloids provide nucleation sites for crystallization of the surrounding glass. If exposed to UV light through a mask, only the exposed regions of the glass will crystallize during subsequent heat treatment at a temperature greater than the glass transformation temperature (e.g., greater than 450° C. in air for FOTURAN). The crystalline phase is more soluble in hydrofluoric acid (HF) than the unexposed vitreous, amorphous regions. In particular, the crystalline regions of Foturan are etched about 20 times faster than the amorphous regions in 10% HF, enabling microstructures with wall slopes ratios of about 20:1 when the exposed regions are removed. See T. R. Dietrich et al., "Fabrication technologies for Microsystems utilizing photoetchable glass," Microelectronic Engineering 30, 497 (1996), which is incorporated herein by reference. FOTURAN is described in information supplied by Invenios (the sole United States source for FOTURAN) as composed of silicon oxide ($SiO_2$) of 75-85% by weight, lithium oxide ($Li_2O$) of 7-11% by weight, aluminum oxide ($Al_2O_3$) of 3-6% by weight, sodium oxide ($Na_2O$) of 1-2% by weight, 0.2-0.4% by weight antimony trioxide ($Sb_2O_3$), silver oxide ($Ag_2O$) of 0.05-0.15% by weight, and cerium oxide ($CeO_2$) of 0.01-0.04% by weight. In some of our etched structures an "APEX-1" composition was used that was composed, by weight, of 71.66% silicon oxide ($SiO_2$), 0.75% boron oxide ($B_2O_3$), 0.4% antimony trioxide ($Sb_2O_3$), 11% lithium oxide ($Li_2O$), 6% aluminum oxide ($Al_2O_3$), 2% sodium oxide ($Na_2O$), 0.15% silver oxide ($Ag_2O$), and 0.04% cerium oxide ($CeO_2$) of by weight, and exposing one portion of the photosensitive glass substrate with ultraviolet light 305 to 315 nm light using an activation exposure of 9 $J/cm^2$, while leaving a second portion of said glass wafer unexposed. The glass substrate was heated to a temperature of 500° C. for one hour and then to a temperature of 600° C. for one hour and then cooled to transform at least part of the exposed glass to a crystalline material. The glass substrate was then etched in an HF-containing etchant solution. Surprisingly, while the composition in the above APEX-1 is similar to Foturan, our experiments with a glass of the above type showed a surprising sensitivity to ultraviolet light exposure of over three times that of the commercially available photosensitive glass (an exposure of 1 $J/cm^2$ was successfully used in a subsequent experiment), and a surprising over six times the etch rate as compared to Foturan when both compositions were processed in the way recommended for Foturan (with the sole exception of the reduced exposure level used for APEX-1 due to its greater sensitivity). Further, our glass had an etch ratio of exposed portion to that of the unexposed portion of about 30:1, while the best reported etch ratio of the commercially available FOTURAN photosensitive glass is about 20:1, using similar processing techniques. It might be that the lower exposure leads to less light scattering into the side walls, and thus less etching of the side walls. The preferred composition modifications of adding boron oxide and reducing the silica content may lead to boron silicate formation that enhances crystallization, but in any case, the results are surprising and unexpected.

Thus photosensitive glass can be processed to provide enhanced adsorption, binding, and attachment of linking chemicals and/or analytes, sensitivity for biological-testing and for directing interrogation light and/or directing fluorescence from a patterned biological-binding area. Thus, the photosensitive glass may have patterned nanoparticles on one side and high precision etched structures on the other (although both could be on the same side).

Patterned glass structures that may be formed include micro-optic lenses, micro-optic micro-posts, and micro-optic waveguides such as micro-channels, micro-ridges (exposed glass is etched away to leave a glass micro-ridge), and index of refraction guides formed by patterned exposure of the glass.

The glass substrate may also be heated to a temperature in excess of the glass transformation temperature to allow at least part of the reduced noble metal to coalesce to provide a patterned glass structure that can be used to form larger clusters for at least one plasmon analytical technique, e.g. surface enhanced fluorescence, surface enhanced Raman spectroscopy, and surface plasmon resonance.

The following APEX design rules may be followed, e.g., using the weight percentages described hereinblow. Boron Oxide and Aluminum oxide basically conduct the same task within the glass melt.

Boron oxide: May also be in the form of anhydride boric acid ($H_3BO_3$), Borax Frits, Gerstley Borate/Colemanite, Boric Acid, Borax, and Ulexite. 13 weight % represents the high end of $B_2O_3$ in borosilicate glasses. Boron Oxide concentration range: Up to 13 weight %.

Aluminum oxide: In the form of Alkali containing feldspars (such as Albite, $NaAlSi_3O_8$) or alumina hydrate. $Al_2O_3$ may be added by using kaolin or nepheline syenite (which contains feldspar) increased viscosity at lower temperatures. Up to weight 7%. This represents the high end of $Al_2O_3$ in borosilicate glasses. These materials prevent or retard crystallization. Aluminum Oxide concentration range: up to 7 weight %. Or more appropriately, the combination of these two should not exceed 13 weight % Potassium Oxide and Sodium oxide help lower the melting point during glass melting.

Potassium oxide: Helps lower melting point. Range up to 16 weight %. May also be Potash ($K_2CO_3$). If used to replace $Na_2O$, typically makes the glass more chemically resistant. Potassium Oxide concentration range: up to 16 weight %.

Sodium oxide: Helps lower the melting point. Range up to 16 weight % (common high end for soda lime glass). May also be soda ash ($Na_2CO_3$) or Glauber's Salt ($Na_2SO_4$). Sodium oxide concentration range: up to 16 weight %. Or more appropriately, the combination of these two should not exceed 16 weight %

Silica: concentration range: 65-85 weight %. Zinc oxide: Improves chemical resistance, lowers thermal expansion, and adds elasticity. Works similarly with CaO. Zinc Oxide concentration range: up to 18 weight %. Lithium Oxide: Aids in nucleation. Can be lithium carbonate. Lithium Oxide concentration range: 8-13 weight %. Cerium Oxide: Electron Donor. Cerium oxide concentration range: up to 0.1 weight %. Antimony trioxide: Oxygen donor. Antimony trioxide (Sb2O3) concentration range: up to 0.4 weight %. Silver Oxide concentration range: up to 5 weight %. Gold Oxide concentration range: up to 5 weight %.

The above ingredients might be at least partially replaced with the following compounds: Calcium Oxide: Improves chemical resistance, lowers thermal expansion, and adds elasticity. Works similarly with ZnO. Up to 18 weight % is used in E-Glass. Calcium Oxide concentration range: up to 18 weight %. Magnesium Oxide: This is the upper end in E-glass and may be in the form of $MgO_2$. Magnesium oxide concentrate range: up to 10 weight %. Barium Oxide Improves refractive index of the material without increasing the dispersive power. Used as a replacement for lead or lime. May also come in the form of $BaCO_3$. Barium Oxide concentration range: up to 18 weight %. Lead Oxide: Improves refractive index of the material with out increasing the dispersive power. Lead Oxide concentration range: up to 18 weight %. Iron may be added to the melt to make the material paramagnetic (e.g. $Fe_2O_3$). Iron oxide may additionally be used to quench intrinsic autofluorescence of other compounds within the glass. Iron Oxide Concentration range: up to 5 weight %.

Processing parameters. Patterning of the selected area(s) by at least one process step selected from: Exposure-Exposing the glass substrate to an activating energy source, such as 310 nm light or a directed source of protons. High surface area capable of biological binding may be obtained using the photoactive glass of the present invention using total activation energy of between 0.4 $J/cm^2$ and 40 $J/cm^2$ of 310 nm light. Baking—Baking typically occurs in a two-step process. Temperature 1 allows for the coalescing of silver ions into silver nanoparticles and temperature 2 allows the lithium oxide to form around the silver nanoparticles. However, we have been successful in doing a single ramp step. Etching—Etching is done in an HF solution, typically 5-10% by volume. However, we can also add other fluids to the etch solution. For example, hydrochloric or nitric acid can be added to the etch solution to obtain a smoother etch because it dissolves the silver nanoparticles. This etch is especially useful in the fabrication of structures and devices that require a smooth surfaces, such as micro-lenses and micro-channels (e.g. to guide fluids). Similar processing with APEX glass can be used to make micro-posts (μPosts), ElectroPosts, micro-optics, micro-lenses, and micro-channels (e.g. wave guides to direct light).

Table 1, below summarizes modern photosensitive glass compositions and various compositions of the present invention. While photosensitive glasses have been known for some time, e.g. patents S. D. Stookey: "Photosensitively Opacifiable Glass" U.S. Pat. No. 2,684,911 (1954), and also U.S. Pat. Nos. 2,628,160 and 2,971,853 covering products sold as Fotoform and Fotoceram, and sometimes described with broad composition ratios, e.g., Speit and U.S. Pat. No. 5,078,771 by Wu (see compositions noted in Table 1), etch ratios apparently have only been evaluated for Foturan, see Dietrich et al. and Livingston, et al., above. Note that for practical purposes anisotropic-etch ratios are easily and accurately measurable. Note also that wall slope angles are difficult to measure directly, e.g. Dietrich et al. give a relatively broad range of 2-4 degrees for their wall slope angle, but that paper also gives a 20:1 etch ratio. As the sine of wall slope angle is equal to the unexposed etch rate divided by the exposed etch rate Dietrich et al.'s wall slope angle can easily calculated from their 1:20 (or 0.05) unexposed to exposed etch ratio, and thus is about 3 degrees (Sine of 3 degrees=0.052). The photosensitive glass composition may also be (in weight percent): less than 72% silica, at least 6% $K_2O$, at least 0.15% $Ag_2O$, at least 0.75% $B_2O_3$, and at least 6% $Al_2O_3$, at least 11% $Li_2O$, and at least 0.04% $CeO_2$; or a composition of: less than 72% silica, at least 0.15% $Ag_2O$, at least 0.75% $B_2O_3$, at least 11% $Li_2O$, and at least 0.04% $CeO_2$. Preferably at least 0.85% $B_2O_3$ is used in some embodiments.

TABLE 1

| Formula | Corning 8603 Fotoform Fotoceram | PEG3 | Schott-Speit on FOTURAN® | Dietrich (commercially available as FOTURAN®) | Pat. No. 5,374,291 | APEX Photosenitive Glass*** (APG) #1 |
|---|---|---|---|---|---|---|
| $B_2O_3$ | | | | | | 0.75 |
| $K_2O$ | 4.10% | 4.00% | | 3-6% | trace** | 5.1 |
| $SiO_2$ | 79.60% | 78.00% | 60-85% | 75-85% | 70-84% | 73.035 |
| $Al_2O_3$ | 4.00% | 6.00% | 2-25%* | 3-6% | 3-10% | 6 |
| $Na_2O$ | 1.60% | 1.00% | | 1-2% | trace** | 2 |
| ZnO | | 1.00% | | 0-2% | trace** | 1.6 |
| $Li_2O$ | 9.30% | 10.00% | 5.5-15%* | 7-11% | 5-20% | 11 |
| $CeO_2$ | 0.014% | 0.080% | 0.001-0.01 | 0.01-0.04% | 0.01-0.1% | 0.035 |
| $Sb_2O_3$ | 0.400% | | | 0.2-0.4% | | 0.35 |
| $Ag_2O$ | 0.11% | 0.080% | 0.0008 to ~0.24* | 0.05 to 0.15% | 0.05 to 0.30% | 0.13 |
| $Au_2O$ | 0.001% | 0.003% | | | | |
| $SnO_2$ | 0.003% | | | | trace** | |
| $As_2O_3$ | | | | | 0.1-0.3% | |
| $Cu_2O$ | | | 0.001-1% | | | |
| other oxides | | | | | trace** | |
| $Al_2O_3:Li_2O$ | | | <1.7 | | | |

| Formula | APG #2 | APG #3 | APG #4 | APG #5 | APG #6 | APG #7 | APG #8 | APG #9 | APG #10 | APG #11 | APG #12 | APG #13 | APG #14 |
|---|---|---|---|---|---|---|---|---|---|---|---|---|---|
| Boron Oxide | 1 | 0.75 | 1.25 | 2 | 0.5 | 0.5 | 0.75 | 0.75 | 1 | 0.5 | 0.5 | 0.5 | 0.75 |
| Potassium Oxide | 6 | 5.5 | 6 | 5 | 4 | 5 | 6 | 5.5 | 6.1 | 5 | 4 | 5 | 5 |
| Silica | 71.48 | 71.84 | 69.16 | 72.03 | 73.45 | 70.68 | 71.66 | 71.7 | 71.56 | 72.57 | 72.21 | 72.96 | 72.21 |
| Aluminum Oxide | 6 | 6 | 6 | 6.25 | 5.5 | 6.25 | 6 | 5.8 | 6.2 | 5.25 | 5.5 | 5.5 | 5.5 |
| Sodium Oxide | 2.5 | 2 | 2 | 1 | 2.25 | 2.5 | 2 | 2 | 1.75 | 2.5 | 2.25 | 2.5 | 2.5 |
| Zinc Oxide | 2.5 | 1.5 | 2 | 2 | 1.5 | 1.25 | 2 | 0.5 | 1.8 | 1.25 | 1.45 | 1 | 1 |
| Lithium Oxide | 10 | 11 | 11 | 10.25 | 11.25 | 11.5 | 11 | 11.5 | 10.5 | 11.5 | 11.5 | 11.5 | 11.5 |
| Cerium Oxide | 0.04 | 0.02 | 0.04 | 0.02 | 0.03 | 0.035 | 0.04 | 0.35 | 0.39 | 0.03 | 0.035 | 0.04 | 0.04 |

TABLE 1-continued

| | | | | | | | | | | | | | |
|---|---|---|---|---|---|---|---|---|---|---|---|---|---|
| Antimonium Trioxide | 0.4 | 0.3 | 0.4 | 0.3 | 0.4 | 0.4 | 0.4 | 0.4 | 0.035 | 0.3 | 0.4 | 0.35 | 0.35 |
| Gold Oxide | 0.08 | 0.04 | | 0.15 | | | 0.15 | | | | | | |
| Silver Oxide | | 0.05 | 0.15 | | 0.12 | 0.14 | | | 0.06 | 0.1 | 0.15 | 0.15 | 0.15 |
| Copper Oxide | | | | | | | | | 0.1 | | | 0.5 | 1 |
| Iron Oxide | | | 1 | 1 | | | | 0.5 | | | | | |
| Calcium Oxide | | 1 | 1 | | | | | 1 | | | | | |
| Barium Oxide | | | | | 1 | 1.75 | | | 0.5 | 1 | 2 | | |

| | Weight % | | | | | | |
|---|---|---|---|---|---|---|---|
| Silica | SiO$_2$ | 71.66 | 58.23 | 78.04 | 62.53 | 71.94 | 74.02 |
| Aluminum Oxide | Al$_2$O$_3$ | 6 | 17.92 | 5.4 | 12.6 | 4.64 | 4.49 |
| Potassium Oxide | K$_2$O | 6 | 4.21 | 4.2 | 4.19 | 5.19 | 4.98 |
| Sodium Oxide | Na$_2$O | 2 | 1.41 | 1.06 | 1.39 | 1.16 | 1.15 |
| Zinc Oxide | ZnO | 2 | 1.35 | 1.63 | 1.95 | 1.92 | 1.83 |
| Antimonium Trioxide | Sb$_2$O$_3$ | 0.4 | 0 | 0 | 0 | 0.46 | 0.47 |
| Silver Oxide | Ag$_2$O | 0.15 | 0 | 0 | 0 | 0.19 | 0.18 |
| Cerium Oxide | CeO$_2$ | 0.04 | 0 | 0 | 0 | 0.04 | 0.04 |
| Iron Oxide | Fe$_2$O$_3$ | 0 | 0.17 | 0.06 | 0.05 | 0 | 0 |
| Lithium Oxide | Li$_2$O$_3$ | 10.79 | 15.66 | 8.14 | 16.46 | 13.16 | 11.14 |
| Boron Oxide | B$_2$O$_3$ | 0.96 | 1.05 | 1.47 | 0.83 | 1.3 | 1.7 |
| Sum | | 100 | 100 | 100 | 100 | 100 | 100 |
| Silica | SiO$_2$ | 74.72 | 74.97 | 71.95 | 73.68 | 66.68 | 73.76 |
| Aluminum Oxide | Al$_2$O$_3$ | 4.42 | 4.32 | 5.63 | 6.75 | 8.58 | 5.46 |
| Potassium Oxide | K$_2$O | 4.91 | 4.81 | 4.55 | 4.08 | 5.32 | 4.43 |
| Sodium Oxide | Na$_2$O | 1.16 | 1.1 | 1.27 | 1.05 | 1.33 | 1.12 |
| Zinc Oxide | ZnO | 1.92 | 1.89 | 1.88 | 1.63 | 2.13 | 1.78 |
| Antimonium Trioxide | Sb$_2$O$_3$ | 0.46 | 0.43 | 0.48 | 0.4 | 0.47 | 0.44 |
| Silver Oxide | Ag$_2$O | 0.18 | 0.17 | 0.2 | 0.15 | 0.22 | 0.17 |
| Cerium Oxide | CeO$_2$ | 0.04 | 0.04 | 0.04 | 0.03 | 0.04 | 0.04 |
| Iron Oxide | Fe$_2$O$_3$ | 0 | 0 | 0.04 | 0.1 | 0.02 | 0.06 |
| Lithium Oxide | Li$_2$O$_3$ | 10.89 | 11.49 | 12.75 | 10.53 | 14.34 | 11.55 |
| Boron Oxide | B$_2$O$_3$ | 1.3 | 0.78 | 1.21 | 1.6 | 0.87 | 1.19 |
| Sum | | 100 | 100 | 100 | 100 | 100 | 100 |

*0.001 to ~0.3 as AgCl
**in some experiments in 5,374,291
***APG = APEX Photosensitive Glass The present invention can also be a method of providing a pattern of biological-binding areas for biological-testing, including selecting areas for metal particles on a transparent substrate; patterning the selected areas by at least one process step selected from the group consisting of; exposing the area to an activating energy source, baking material having a glass transition temperature at a temperature above the glass transition temperature, etching the areas to expose portions of metal particles or nearly expose metal particles from within a transparent solid; and depositing patterned areas of biological-binding-transparent solid on a substrate; and attaching biological molecule to the selected areas.

In addition, the present invention may be used in conjunction with labels, chromophores, one or more luminescent compounds and fluorophore known to the skilled artisan, e.g., cresyl fast violet, cresyl blue violet, rhodamine-6G, para-aminobenzoic acid, phthalic acids, erythrosin or aminoacridine. In addition, fluorophore or fluorescent reporter groups may be used and include any compound, label, or moiety that absorbs energy, typically from an illumination source, to reach an electronically excited state, and then emits energy, typically at a characteristic wavelength, to achieve a lower energy state, e.g., fluorescein and its derivatives; rhodamine and its derivatives; cyanine and its derivatives; coumarin and its derivatives; CASCADE BLUE and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa Fluor 488, Alexa Fluor 532, Alexa Fluor 546, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate, carboxy-fluorescein, phycoerythrin, rhodamine, dichlororhodamine, carboxy tetramethylrhodamine, carboxy-X-rhodamine, PicoGreen, RiboGreen, and the like. Descriptions of fluorophores and their use, can be found in, among other places, R. Haugland, Handbook of Fluorescent Probes and Research Products, 9.sup.th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va. Near-infrared dyes are expressly within the intended meaning of the terms fluorophore and fluorescent reporter group.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

It will be understood that the above description is merely illustrative of the applications of the principles of the present invention, the scope of which is to be determined by the claims viewed in light of the specification. Other variants and modifications of the invention will be apparent to those of skill in the art.

References

1. Lakowicz, et al; "Advances in Surface-Enhanced Fluorescence", Journal of Fluorescence, Vol. 14 No. 4, July 2004 pp. 425-441.

2. Chowdhury, et al, J Fluorescence, "Metal-Enhanced Chemiluminescence", (2006) 16:295-299.

3. "Silica Microspheres" TechNote #104, Bangs Laboratories, Fishers, I N, 46038-2886, 1-800-387-0672.

4. "Covalent Coupling" TechNote #205, Bangs Laboratories, Fishers, I N, 46038-2886, 1-800-387-0672.

5. Aslan, et al, "Metal-Enhanced Fluorescence: an emerging tool in biotechnology" Analytical biotechnology; Current opinion in Biotechnology 2005, 16:55-62.

6. Geddes, et al, "Metal-Enhanced Fluorescence" Journal of Fluorescence, Vol. 12 No. 2, June 2002, pp 121-129.

7. "Working with Microspheres" TechNote #201, Bangs Laboratories, Fishers, I N, 46038-2886, 1-800-387-0672.

What is claimed is:

1. A method of forming one or more metallic areas on a substrate for biological-testing, comprising the steps of:
   providing a photosensitive glass-ceramic substrate comprising a photosensitive glass-ceramic substrate and one or more metal containing compounds selected from metal oxides, metal nanoparticles, metal alloys, and atomic metals with a range of diameters that are less than about 300 nanometers and are spaced an average distance of at least one-half the midpoint of the diameter range apart;
   activating at least a portion of the photosensitive glass-ceramic substrate to form a pattern;
   heating the photosensitive glass-ceramic substrate to a temperature near a glass transformation temperature of the photosensitive glass-ceramic substrate to form one or more congregated metal nanoparticles in the photosensitive glass-ceramic substrate;
   baking the photosensitive glass-ceramic substrate to convert the one or more congregated metal nanoparticles into one or more metallic biological-binding areas; and
   etching the photosensitive glass-ceramic substrate to expose the one or more metallic biological-binding areas with an enhanced adherence to biological molecules.

2. The method of claim 1, further comprising the step of applying a pattern mask by screen printing, photolithography or a combination thereof on at least a portion of the photosensitive glass-ceramic substrate to protect from activation.

3. The method of claim 1, further comprising the step of applying an etching pattern mask by screen printing, photolithography or a combination thereof on at least a portion of the photosensitive glass-ceramic substrate to protect from etching.

4. The method of claim 1, wherein the step of activating comprises exposing to an UV activating energy source.

5. The method of claim 1, wherein the one or more metal containing compounds comprise silver, gold, platinum, rhodium, palladium, nickel, cobalt, copper, or alloys or combinations thereof.

6. The method of claim 1, wherein the one or more metal oxides are exposed to high-energy particles to reduce the one or more metal oxides to one or more metal nanoparticles.

7. The method of claim 1, wherein the one or more congregated metal nanoparticles are formed by metal-precipitating one or more metal nanoparticles from metal oxides.

8. The method of claim 1, wherein the one or more congregated metal nanoparticles are assayed by techniques using surface plasmon excitation.

9. The method of claim 8, wherein one or more congregated metal nanoparticles undergo analysis by surface enhanced fluorescence (SEF), metal enhanced fluorescence (MEF), surface enhanced Raman scattering (SERS), surface plasmon resonance (SPR) or surface enhanced resonance Raman scattering (SERRS).

10. The method of claim 1, further comprising the step of contacting one or more biological molecules to the one or more ceramic biological-binding areas, wherein the one or more biological molecules comprise one or more chromophores, one or more fluorophore, one or more luminescent compounds, one or more radioactive labels or a combination thereof 11. The method of claim 1, further comprising the step of attaching one or more biological molecules to the one or more metallic biological-binding areas and contacting the one or more biological molecules with a target molecule wherein the target molecule, the one or more biological molecules or both independently comprise one or more DNA, RNA, PNA, proteins, peptides, carbohydrates, lipids, ligands, enzymes, phage antibody-display, ribosome display, kinases, drugs, receptors, hapten, pathogen, toxin, hormone, chemicals, liposomes, carbohydrate, organic compounds, compounds containing at least one non-binding electron pair, other biological compounds or combinations thereof.

12. The method of claim 1, wherein the one or more metal containing compounds are added as one or more metal particles during fabrication of the photosensitive glass-ceramic substrate.

13. The method of claim 1, wherein the one or more metal containing compounds are added as a metal salt during fabrication of the photosensitive glass-ceramic substrate.

14. The method of claim 1, further comprising the step of contacting one or more biological molecules to the one or more metallic biological-binding areas wherein the one or more biological molecules.

15. The method of claim 14, further comprising the step of contacting one or more second biological molecules to the one or more second biological molecules to form a capture detect assay, wherein the one or more second biological molecules comprise one or more DNA, RNA, PNA, proteins, peptides, carbohydrates, lipids, ligands, enzymes, phage antibody-display, ribosome display, kinases, drugs, receptors, hapten, pathogen, toxin, hormone, chemicals, liposomes, carbohydrate, organic compounds, compounds containing at least one non-binding electron pair, other biological compounds or combinations thereof.

* * * * *